United States Patent [19]
Crangle

[11] Patent Number: 5,483,974
[45] Date of Patent: Jan. 16, 1996

[54] DEVICE TO APPLY, HOLD, AND MEASURE CRICOID PRESSURE DURING ENDOTRACHEAL INTUBATION OR CRICOTHYROIDOTOMIES, OR OTHER MEDICAL AIRWAY PROCEDURES

[76] Inventor: Richard Crangle, 204 Sports Mall Plaza 1, 5505 S. 900 East, Salt Lake City, Utah 84117

[21] Appl. No.: 63,737

[22] Filed: May 20, 1993

[51] Int. Cl.⁶ .................................................. A61B 5/103
[52] U.S. Cl. .................................... 128/774; 606/202
[58] Field of Search .................................. 128/774, 777, 128/782; 606/201–203

[56]  References Cited

U.S. PATENT DOCUMENTS

| | | | |
|---|---|---|---|
| 2,714,379 | 8/1955 | Raines | 606/202 |
| 3,279,459 | 10/1966 | Schenker | 606/202 |
| 4,210,147 | 7/1980 | Nestor et al. | 606/202 |
| 4,592,371 | 6/1986 | Pellicano et al. | 128/774 |
| 4,989,615 | 2/1991 | Hochberg | 128/774 |
| 5,131,408 | 7/1992 | Smith | 128/774 |
| 5,181,522 | 1/1993 | McEwen | 128/774 |

*Primary Examiner*—Max Hindenburg
*Attorney, Agent, or Firm*—Dennis L. Mangrum

[57]  ABSTRACT

A mechanical device for applying a constant pressure/force to the cricoid cartilage during endotracheal intubation or other medical airway operations/procedures. The device has a contact surface that is disposed directly against the neck, above the cricoid cartilage of the patient, and held in place by an adjustable strap that passes behind the patient's neck and is secured to the protruding or cantilevered ends of the device. The device and strap are used to create pressure/force only on the back and front of patient's neck. The contact surface is held in place and transfers the force to a compressible bladder contained in the device. The strap can be adjusted until proper cricoid pressure is achieved for the intubation and then held in place to maintain the pressure until the procedure is concluded. The safety valve prevents excessive force application.

12 Claims, 1 Drawing Sheet

DEVICE TO APPLY, HOLD, AND MEASURE CRICOID PRESSURE DURING ENDOTRACHEAL INTUBATION OR CRICOTHYROIDOTOMIES, OR OTHER MEDICAL AIRWAY PROCEDURES

BACKGROUND OF THE INVENTION

1. Field of the Invention

The present invention is a mechanical device to be used by trained medical physicians during medical procedures such as intubation of the trachea or other medical airway operations/procedures to maintain the cricoid pressure at a constant value during the procedure.

2. Prior Art

There are no known mechanical devices to assist a physician to maintain cricoid pressure during an endotracheal intubation or other related medical airway operation procedure. The only known method presently recognized or employed to maintain cricoid pressure during intubation of the trachea is to have a specially trained physician apply hand or finger pressure to the cricoid cartilage while an assisting physician completes the intubation. Endotracheal intubation involves advancing an endotracheal tube through the pharyngeal area into the trachea to ventilate the lungs.

Intubation of the trachea using various kinds of tracheal airways is frequently performed by medical personnel in a broad range of medical areas including anesthesiology, intensive and critical care, trauma surgery, emergency rooms, emergi-centers, and pre-hospital care. After successful intubation, the patient is ventilated with manual or mechanical air supplies.

There is a high risk of aspiration of gastric contents into the lungs during intubation or cricothyroidotomies because the cricoid pressure increases and thereby creates an imbalance between the lungs, stomach and interconnected passages. This imbalance causes gastric contents to be aspirated into the lungs, and resulting aspiration pneumonitis, which most often is fatal to the patient. The solution of the problem is to precisely manipulate and maintain cricoid pressure to counteract reduction in esophageal sphincter pressure (OSP) and prevent regurgitation into the lungs, during intubation.

Recent medical literature recognizes that gastric aspiration is a frequently encountered problem, and strongly recommends application of cricoid pressure on all patients during these procedures. However, practitioners do not have a mechanical device available to properly measure, manipulate or maintain the cricoid cartilage pressure. The recommended procedure is to have a physician apply the proper amount of pressure until the airway is properly placed. Medical attendants employing this technique are carefully trained to be able to guess or estimate the amount of pressure being applied to the cricoid cartilage by hand and finger pressure on the patient's trachea. The proper cricoid pressure is known to be between 27 to 30 newtons for a conscious patient and between 38 to 40 for an unconscious patient. The trained attending physician is supposed to be able to estimate, due to his training, and to maintain the precise force as intubation is occurring without distortion of the trachea. Unfortunately, too much or too little force/pressure may put the patient at risk. The two-fold risk is from: too much pressure which may damage the trachea or surrounding anatomical structures and distort the airway thereby producing inadequate patient ventilation; or, too little pressure, which obviates the efficacy of the procedure by failing to alter esophageal pressure enough to prevent aspiration of gastric contents.

Studies performed at St. Thomas Hospital, London, England and published in *Anesthesiology* 1992, V47 indicate the absolute necessity of maintaining proper levels of cricoid pressure needed during intubation procedures. That article indicates that the only 'safe' method is to use two medical attendants, one to apply the cricoid pressure and the other to perform the intubation. The article also identifies the exact pressure to be applied to the cricoid, but does not propose any method for measuring or maintaining that pressure.

In the Journal of the American Medical Association Standards for CPR and ECC, page 2935, the procedure to performing intubation is specified:

"Cricoid pressure requires a second person and should be applied, when possible, during endotracheal intubation to protect against regurgitation of gastric contents, as follows: to find the anatomic landmark, palpate the depression just below the thyroid cartilage (Adam's apple). This depression is the cricothyroid membrane; the prominence inferior to that is the cricoid cartilage. Pressure should be applied to the anterolateral aspects of the cartilage just lateral to the midline. This pressure is applied with the thumb and index fingers of either hand. A higher degree of pressure is required to prevent regurgitation than to prevent gastric distention. The pressure on the cricoid should be maintained until the cuff of the endotracheal tube is inflated." (*Standards for CPR and ECC,* JAMA, Vol. 255. No. 21, p. 2935.)

In Anesthesia, by Ronald D. Miller, M.D. Vol 2, some of the attendant problems and solutions are identified.

"Cricoid pressure is the simplest and most effective measure for minimizing the risk of aspiration. However, the person applying cricoid pressure must know how to do so properly. Pressure is applied at the cricoid cartilage, not the thyroid cartilage or over the entire larynx. Pressure applied to the thyroid cartilage makes the intubation process more difficult, whereas pressure applied to the cricoid cartilage makes endotracheal intubation easier. Some prefer to place one hand behind the patient's neck while applying pressure at the cricoid cartilage. In addition to ensuring proper placement of pressure, the attendant must not release the pressure until the intubation is complete and the cuff inflated.

It is very tempting when things go awry during rapid sequence induction for the attendant applying cricoid pressure to help by picking up a dropped endotracheal tube, finding a stylet, correcting an intravenous needle placement, or even removing false teeth or other material from the mouth. It is at this precise time that regurgitation and aspiration can and most likely will occur. Maternal mortality studies from England demonstrate that in 7 or 11 cases of aspiration that occurred during caesarean section, the person applying cricoid pressure had applied it inappropriately or had released it before the intubation was complete. Applied properly, cricoid pressure should prevent nearly all cases of aspiration." (*Management of Aspiration Pneumonitis,* Gibbs and Modell, p. 1311.)

In the *Medical Journal Digest* Volume 75, May 5, 1979, a study to evaluate intubation indicated that: "the department or level of training of the intubator did not affect the ratio of complications . . . " It is obvious that even a trained physician can not apply and maintain the proper pressure without some method of determining the cricoid pressure during intubation.

In *Respiratory Care,* 1990, 5th edition, page 450, it was noted:

One out of three patients with gross aspiration that progresses to pneumonia will die as a result of that condition.

Eighty percent (80%) of all patients with tracheostomies have one or more episodes of aspiration . . .

Massive aspiration leads to cardiac arrest . . .

Because of the high risk of aspiration pneumonitis, all pregnant patients receiving general anesthesia must be considered to have a full stomach. Therefore, use of a rapid-sequence induction, with cricoid pressure until the airway has been secured with a cuffed endotracheal tube, is preferred.

Intubation is a very advanced medical procedure that can result in severe harm to a patient, should things go wrong. The problem of measuring and maintaining cricoid pressure has been identified. The present invention overcomes all of these problems by providing an accurate, reliable mechanical device capable of exerting and maintaining precise cricoid pressure during the entire intubation process. It also permits the procedure to be completed by one physician.

SUMMARY OF THE INVENTION

A mechanical device to be used during endotracheal intubation or cricothyroidotomies that will create and maintain precise cricoid pressure during the procedure, is disclosed. The contact surface of the mechanical device is placed directly on the cricoid cartilage anatomical site and appropriate pressure is applied as indicated by the pressure measuring gauge, which derives its readings from a pressure bladder in the housing activated when the device is depressed against the cricoid cartilage. The pressure/force is created and/or maintained by manipulating the adjustable strap disposed around the neck of the patient and attached to the projecting or cantilevered ends of the housing. Upon reaching the desired pressure level, the strap is secured in place. The gauge and pressure assembly prevent application of pressure above recommended limits by visually displaying the pressure and by utilizing a pressure relief valve. After the airway is established, and intubation completed, the relief valve can also be activated to release pressure and the device is easily removed.

It is an object of the invention to provide a contact surface that is easily replaceable which contacts the patients neck and can be discarded after every use and permits the device to be cleaned with standard known sterilization procedures.

It is an object of the invention to provide a neck strap that is easily and adjustably secured in place during use with hook and loop, or other known fastening means, that is easily cleaned and or replaced.

It is an object of the invention to provide a device that can be employed on conscious and unconscious patients.

DETAILED DESCRIPTION OF THE PREFERRED FORM OF THE INVENTION

Figure 1:
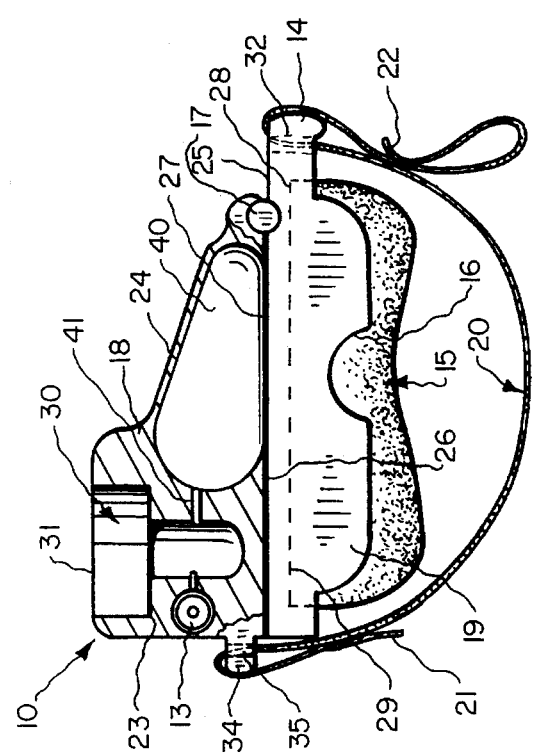
FIG. 1 is a side view showing the device with pressure application assemblies including hinged housing, compressible bladder, relief valve, contact surface, and holding assembly.

In FIG. 1 the preferred form of the present invention is shown. It is understood that modifications can be made to the presently preferred form without departing from the spirit and substance of the invention. The preferred form is described hereinafter to illustrate the invention.

The rigid housing 10 serves to contain the bladder 40, the pressure dial indicator 30, relief valve 13 and the contact surface 15. Housing 10 is comprised of a first section 18, and a second section 19 that are hinged about pivot pin 17. The first section has a receptacle 23 disposed toward one end into which a pressure dial 30 is disposed. The pressure dial 30 is well known and typical, and is in turn connected to pressure relief valve 13, also well known, and bladder 40 by means of manifold 41, FIG. 1. Bladder 40 is held and contained in section 1 and disposed in cavity 24. Cavity 24 is defined to encase the bladder but has an opening 27 in cooperation with surface 25 to permit the bladder to engage surface 26 of section 2 of housing 10. Section 1 has one end 34 projecting beyond housing 10 to cantilever or protrude from the end of the housing (FIG. 1). An aperture 35 is disposed at the end of end 34 and is capable of having a strap 20 disposed therethrough.

Section 2 of housing 10 has a cavity 28 therein into which the contact surface 15 can be disposed. Cavity 28 has a surface 29, flat and approximately parallel to surface 26 onto which contact surface 15 can be secured by tape or other temporary securing means. The end 14 of section 1 is cantilevered and protrudes from the basic body of housing 10 as shown in FIG. 1, and has an aperture 32 disposed toward the outermost end, that is capable of having strap 20 disposed therethrough. Section 1 and section 2 are hinged about pivot 17 such that when surface 25 of section 1 and surface 26 are forced together they create pressure in bladder 40 which pressure is indicated in dial 30.

Strap 20 is capable of being adjustable and securely fastened to end 34 of section 1, and end 14 of section 2.

Figure 2:
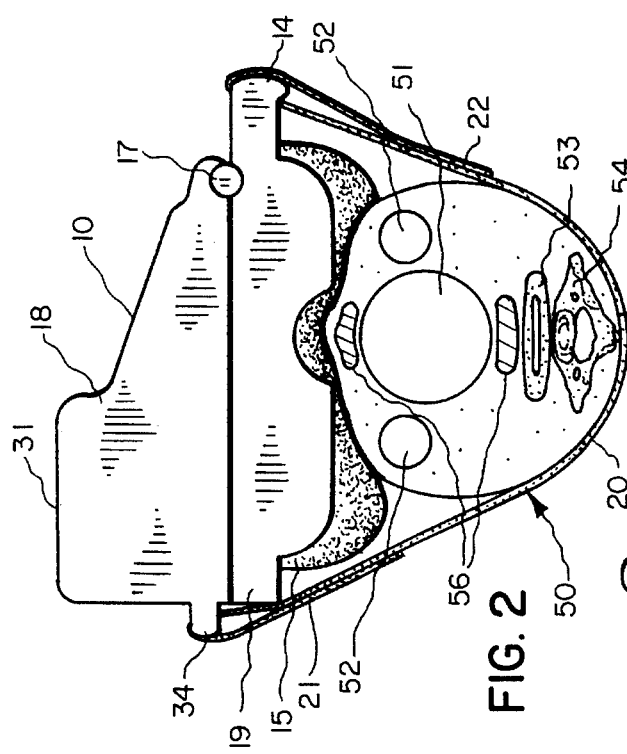
FIG. 2 is a top view showing the pressure gauge assembly integrated into the face of the housing.
Figure 3:
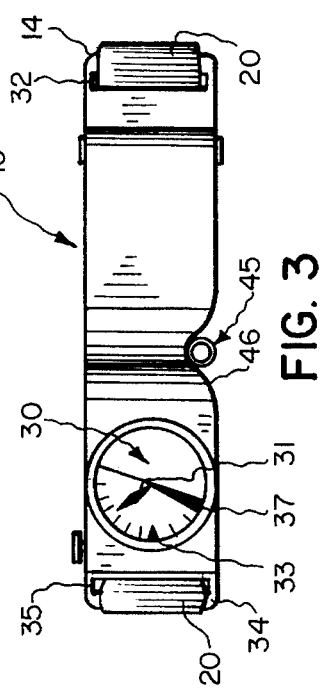
FIG. 3 is a sagittal longitudinal sectional view of the device in place on the neck of a patient.

The mechanical device described above is employed by being placed on the patient's neck 50 as shown in FIGS. 2 & 3, with the housing 10 being disposed on the cricoid cartilage 56. The strap 20 is disposed around the patient's neck 50. Strap 20 will only contact the back of the patient's neck and engaged the ends 14 & 34 of the device (FIG. 2). The cantilevered ends 14 and 34 extend far enough beyond the patient's neck to only permit pressure to be applied to the back of the neck and on the contact surface 15, thereby eliminating circumferential pressure (which is medically undesirable) on the neck 50. In the preferred embodiment the cantilevered projections extend one inch beyond the patient's neck on either side, although the only requirement of the invention is to eliminate circumferential pressure.

Due to the cantilevered extension of the device, pressure is exerted directly down on the anterior aspect of the cricoid cartilage 56 and on the directly opposite posterior aspect of the patient's neck 50. This prevents circumferential pressure which may cause excessive pressure on the major vessels 52 of the neck 50. A compressible bladder 40 which can be either air or liquid filled is shown in FIG. 1. In the preferred form, air is used. When the device is employed, FIG. 2, surface 26 of section 1 engages bladder 40 creating pressure against the cricoid cartilage and that pressure is translated to pressure indicator 30 through the connecting manifold 41 which directs pressure from the distensible bladder 40 to both the relief valve 13 and to dial indicator 30. The dial indicator is also marked, FIG. 3, to indicate maximum allowable pressure 37 as well as actual pressure 31 prevent continued observation of the actual cricoid pressure. A redundant safety feature of the device is achieved by clear markings on the gauge indicating maximum pressures for either the conscious maximum mark 37 or the unconscious maximum mark 33 patient. The relief valve 13 used to depressurize the compressible bladder 40 will automatically release pressure at any time the maximum predetermined pressure values are exceeded. Since the esophageal sphincter 53 pressure values are significantly different for the conscious and the unconscious patient, recommended cricoid pressure needs to be properly applied for these two categories of patients. Accordingly, the current invention has clear indication on the dial of the pressure indicator 30. In FIG. 2 device shows desired pressure value for the conscious patient 37 and another indicated value for the unconscious patient 33.

Figure 4:
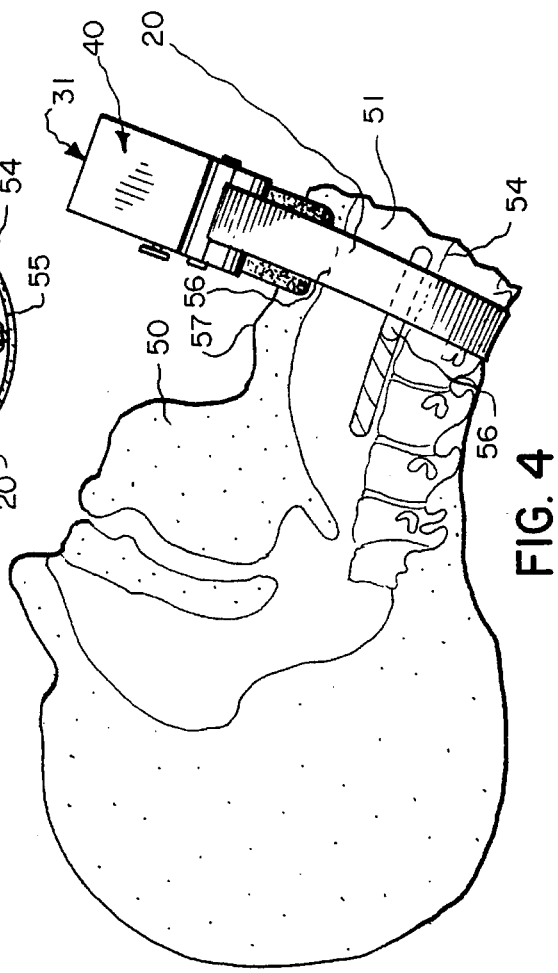
FIG. 4 is a cross sectional view showing the mechanical device in place on a patient prior to intubation.

In application, the device is placed directly on the anterior aspect of the cricoid cartilage 56 as shown in FIG. 4. The depression 16 in the contact surface 15 is adapted to fit about the patient's neck without interfering with breathing or the thyroid cartilage 57 (Adam's Apple) FIG. 2. The strap 20 is disposed around the patient's neck, FIG. 2, with end 21 secured by means of hook and loop fastener or any other fastener well known in the art could be utilized. Once in place the end of holding strap assembly 22 is threaded through aperture 34 of end 14 of the housing. Hand pressure is then applied to the device until the required pressure is achieved. Strap end 22 is then secured in place by hook and loop or another fastening means to maintain the precise pressure. The pressure on the cricoid cartilage 56 depresses the cricoid cartilage 56 to occlude the esophagus 53, and maintain the desired pressure in the esophagus, thereby preventing gastric reflux and aspiration of gastric contents. Once the predetermined pressure is achieved it can be maintained during the duration of the airway management operation.

Having now described the preferred form of the device of the present invention and it's operation, additional features of the invention will be described.

The contact surface 15 is formed from a medium stiff dense foam material. It has disposed on the non-patient contact edge a double sided tape. The tape secures the foam to surface 29 of the cavity 28 of section two and holds it in place. The entire contact surface can be removed, discarded, and replaced after use with a new contact surface 15. Easy removal of the contact surface permits the device 10 to be sterilized by known techniques, a new contact surface inserted and the device reused numerous times.

Rigid housing 10 is formed of highly resilient plastic in the preferred form and can be cleaned after each use with standard sterilization equipment such as an autoclave. The strap 20 in the present invention formed of a rip-stop nylon webbing or comparable material, that can be cleaned and/or discarded and replaced after each use. The device can be quickly readied for reuse. It is durable, and easy to sterilize after each use with standard well known sterilization procedures.

In an alternate embodiment of the invention the bladder and pressure sensing system could be replaced with an electronic pressure sensing device, and the dial indicator replaced with an electronic display. In effect, the device could be made to be totally electronic with warning buzzers and the like, and still be within the spirit and scope of the invention.

Sometimes during an endotracheal intubation procedure, it becomes necessary to perform an cricothyroidotomy immediately. Such a procedure requires a puncture to be performed precisely through the cricoid thyroid ligament of the patient. Locating the precise point is critical and is particularly difficult in emergency situations. The present invention holds to resolve that situation by providing a guide or slot 46, built into the superior aspect side of the device, (see FIG. 2) and can be used without affecting the application, measurement, or maintenance of cricoid pressure. This slotted guide 46 serves to guide the surgical instrument 45, FIG. 3 during cricothyroidotomy, to prevent the surgical instrument 45 from slipping in a lateral direction. The device 10 when properly placed, precisely locates the puncture point directly below the slotted guide 45.

The device has also been found to be extremely valuable when performing endotracheal intubation on animals. For instance ruminant animals like goats have extreme regurgitation problems when subjected to intubation. The device of the present invention has been shown to be almost completely effective to eliminate such regurgitation problems.

I claim:

1. A device to apply, hold, and measure cricoid pressure during endotracheal intubation, cricothyroidotomies, or other medical airway procedures comprising:

a means for applying a force to the cricoid cartilage of a patient, a pressure sensitive gauge attached to said means for applying pressure, said pressure sensitive gauge capable of measuring said force applied to said cricoid cartilage, and, a means for selectively maintaining a predetermined Force to the cricoid cartilage, whereby said force is applied to the cricoid cartilage by said means for applying said force until said predetermined force is reached wherein said means for selectively maintaining said force at said predetermined increment is employed during the medical airway management procedure.

2. A mechanical device for applying a force to the cricoid cartilage of a patient, for measuring said force, and for maintaining said force at a predetermined level during an endotracheal intubation, or cricothyroidotomy or medical airway management procedure without distortion of airway, said mechanical device comprising;

a lightweight rigid housing having a first and a second section pivoted about one end, said first section containing a means for measuring the force exerted against said first section by said second section, said second section capable of retaining a pad to contact a patient's neck near the cricoid cartilage, the ends of said housing projecting beyond the patient's neck;

a strap capable of being adjustably connected to said projecting ends of said housing and for encircling the patient's neck, for creating a Force on the cricoid cartilage as said strap is adjustably tightened and maintained once said predetermined force is achieved;

whereby said device may be disposed on the cricoid cartilage of the patient's neck, said strap disposed around the patient's neck and engaging said projecting ends of said housing and the back of the patient's neck, and said strap for being adjusted to create said predetermined force as indicated by said means for measuring said force on the cricoid cartilage and to maintain said predetermined force during said medical airway management procedure.

3. The mechanical device of claim 2 wherein said housing is formed from lightweight rigid plastic said first section for containing a compressible bladder for engaging said second section as said strap is adjusted to create a force between said 1st and 2nd sections, said Force comparable to the force exerted on the patient's cricoid cartilage; said bladder connected to a dial indicator to display the force being applied to the cricoid cartilage.

4. The mechanical device of claim 3 wherein a safety relief valve having a preset release point is coupled to said bladder to prevent the application of excess force against the cricoid cartilage.

5. The mechanical device of claim 2 wherein said means for measuring the force between said 1st and 2nd sections of said housing is electronic.

6. The mechanical device of claim 2 wherein said strap is formed from rip-stop nylon and is easily replaceable.

7. The mechanical device of claim 2 wherein said pad is formed from a poly foam substance and is removably secured to said second section of said housing so as to be discarded after each use and permit said device to be sterilized by standard well known procedures.

8. The mechanical device of claim 2 wherein said second section is formed to prevent engagement with the patient's carotid vessels during use.

9. The mechanical device of claim 8 wherein a grooved cut-out impression is disposed into and through said first and second section to guide surgical instruments directly to the desired anatomical puncture point for performance of an cricothyroidotomy.

10. The mechanical device of claim 2 wherein said strap is adjustably secured with hook and loop fasteners.

11. The mechanical device of claim 2 wherein said means for measuring said force between said 1st and 2nd sections of said housing comprises a bladder and dial indicator capable of displaying said force applied to the cricoid cartilage in pressure increments and capable of displaying said pressure to the user.

12. The mechanical device of claim 1 wherein said dial indicator has displayed thereon predetermined safety maximum and minimum pressure levels that may be achieved during said medical procedure.

\* \* \* \* \*